(12) United States Patent
Fujii et al.

(10) Patent No.: US 9,232,899 B2
(45) Date of Patent: Jan. 12, 2016

(54) BLOOD PRESSURE INFORMATION MEASUREMENT DEVICE AND CONTROL METHOD OF BLOOD PRESSURE INFORMATION MEASUREMENT DEVICE

(75) Inventors: Kenji Fujii, Kyoto (JP); Tatsuya Kobayashi, Shiga (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 694 days.

(21) Appl. No.: 13/565,330

(22) Filed: Aug. 2, 2012

(65) Prior Publication Data

US 2012/0296223 A1 Nov. 22, 2012

Related U.S. Application Data

(63) Continuation of application No. PCT/JP2010/072771, filed on Dec. 17, 2010.

(30) Foreign Application Priority Data

Feb. 2, 2010 (JP) ................................ 2010-021245

(51) Int. Cl.
*A61B 5/0225* (2006.01)
*A61B 5/021* (2006.01)
*A61B 5/022* (2006.01)
*A61B 5/0235* (2006.01)

(52) U.S. Cl.
CPC ............ *A61B 5/0225* (2013.01); *A61B 5/022* (2013.01); *A61B 5/02125* (2013.01); *A61B 5/02141* (2013.01); *A61B 5/0235* (2013.01); *A61B 5/02233* (2013.01)

(58) Field of Classification Search
CPC .. A61B 5/0225; A61B 5/02141; A61B 5/022; A61B 5/02125; A61B 5/02233; A61B 5/0235
See application file for complete search history.

(56) References Cited

U.S. PATENT DOCUMENTS

2010/0268092 A1 10/2010 Kobayashi et al.

FOREIGN PATENT DOCUMENTS

| JP | 2003204945 A | 7/2003 |
| JP | 2004-113593 A | 4/2004 |
| JP | 2004-195071 A | 7/2004 |
| JP | 2007-522857 A | 8/2007 |

(Continued)

OTHER PUBLICATIONS

International Search Report issued in PCT/JP2010/072771 mailing date Jan. 18, 2011, and English translation thereof (4 pages).

(Continued)

*Primary Examiner* — Michael Kahelin
*Assistant Examiner* — Tho Tran
(74) *Attorney, Agent, or Firm* — Osha Liang LLP (57) ABSTRACT

A measurement device pressurizes two cuffs in a state in which the cuffs are attached to the distal side and the proximal side of the measurement device, respectively, calculates an AI value or the like based on a pulse wave detected from a change in cuff pressure on the distal side while pressurizing the two cuffs, and determines that avascularization on the distal side has been completed if the AI value or the like has converged. Once it is determined that avascularization has been completed, the cuff pressure on the distal side is fixed, and a pulse wave is detected from a change in cuff pressure on the proximal side in a state in which the distal side is avascularized.

6 Claims, 9 Drawing Sheets

(56) References Cited

FOREIGN PATENT DOCUMENTS

| | | | | |
|---|---|---|---|---|
| JP | 2009119067 A | 6/2009 | | |
| JP | 2009-284965 | * 10/2009 | ............... | A61B 5/02 |
| JP | 2009-284965 A | 12/2009 | | |
| JP | 2009297222 A | 12/2009 | | |
| JP | 2010099385 A | 5/2010 | | |
| WO | 2009/063939 A1 | 5/2009 | | |
| WO | 2009/145027 A1 | 12/2009 | | |

OTHER PUBLICATIONS

Patent Abstracts of Japan, Publication No. 2004-113563, publication date Apr. 4, 2004 (1 page).

Patent Abstracts of Japan, Publication No. 2004-195071, publication date Jul. 15, 2004 (1 page).

Patent Abstracts of Japan, Publication No. 2003-204945, publication date Jul. 22, 2003 (1 page).

Patent Abstracts of Japan, Publication No. 2009-119067, publication date Jun. 4, 2009 (1 page).

Patent Abstracts of Japan, Publication No. 2009-297222, publication date Dec. 24, 2009 (1 page).

Patent Abstracts of Japan, Publication No. 2009-284965, publication date Dec. 10, 2009 (1 page).

Patent Abstracts of Japan, Publication No. 2010-099385, publication date May 6, 2010 (1 page).

* cited by examiner

BLOOD PRESSURE INFORMATION MEASUREMENT DEVICE AND CONTROL METHOD OF BLOOD PRESSURE INFORMATION MEASUREMENT DEVICE

TECHNICAL FIELD

The present invention relates to a blood pressure information measurement device and a control method of the blood pressure information measurement device, and particularly relates to a blood pressure information measurement device that uses a cuff and a control method of the blood pressure information measurement device.

BACKGROUND ART

As disclosed in JP 2004-113593A (hereinafter referred to as Patent Literature 1), there is a technology of measuring a pulse wave on the heart side while the distal side is avascularized, thereby separating an ejection wave ejected from the heart and a reflection wave reflected from the iliac artery bifurcation and a sclerotic site in an artery, and calculating and determining an arteriosclerosis index based on the amplitude difference, the amplitude ratio, the appearance time difference, or the like between those waves.

With regard to avascularization on the distal side, JP 2004-195071A (hereinafter referred to as Patent Literature 2), JP 2003-204945A (hereinafter referred to as Patent Literature 3), and JP 2007-522857T (hereinafter referred to as Patent Literature 4) disclose technologies of precisely detecting a characteristic point of the ejection wave and a characteristic point of the reflection wave by compression with a higher pressure than the systolic blood pressure. The applicant of the present invention also discloses in JP 2009-119067A (hereinafter referred to as Patent Literature 5) a technology of enabling calculation of a precise arteriosclerosis index by measuring a sharp pulse wave in a state in which the distal side is avascularized with two cuffs, one each on the distal side and the proximal side.

The technologies disclosed in Patent Literature 1 and the like compress a measurement site of a subject over the skin using an air bladder called a cuff, thereby compressing an artery at the measurement site. According to these technologies, the artery is compressed by pressing the cuff against the measurement site of the subject with a constant pressing force. For example, Patent Literature 4 discloses that this constant pressing force is +35 mmHg, which is a systolic blood pressure value of a subject.

Patent Literature 1: JP 2004-113593A
Patent Literature 2: JP 2004-195071A
Patent Literature 3: JP 2003-204945A
Patent Literature 4: JP 2007-522857T
Patent Literature 5: JP 2009-119067A

SUMMARY OF INVENTION

However, the rate at which the cuff pressure is transferred to the artery varies depending on physical characteristics of the subject, such as the amount of muscle, the amount of fat, and the depth of the artery. For this reason, even when the cuff is pressed against the measurement site of the subject with a constant pressing force, there are cases where the cuff pressure is transferred to the artery at a lower rate than expected depending on the physical characteristics of the subject. In such cases, compression is insufficient, a precise pulse wave measurement cannot be performed.

Alternatively, there are cases where the cuff pressure is transferred to the artery at a higher rate than expected depending on the physical characteristics of the subject. In such cases, the measurement time is prolonged, and the burden on the subject increases.

Therefore, one or more embodiments of the present invention provide a blood pressure information measurement device capable of accurately measuring blood pressure information and a control method of the blood pressure information measurement device.

According to one or more embodiments of the present invention, a blood pressure information measurement device is a blood pressure information measurement device for measuring blood pressure information of a subject and includes a first fluid bladder, a second fluid bladder, a coupling unit that switches between a coupled state in which the first fluid bladder and the second fluid bladder are coupled to each other so that communication of a fluid inside the fluid bladders is allowed and an uncoupled state in which the coupled state of the fluid bladders is released so that communication of the fluid is not allowed, an adjustment unit that adjusts internal pressures of the first fluid bladder and the second fluid bladder, a pressure sensor that measures the internal pressures of the first fluid bladder and the second fluid bladder, and a computation unit that calculates blood pressure information based on a change in the internal pressure of each of the first fluid bladder and the second fluid bladder attached to a measurement site. The computation unit executes a computation that determines an avascularized state on a distal side of the measurement site, based on a change in the internal pressure of at least one of the first fluid bladder and the second fluid bladder during a process by which the first fluid bladder and the second fluid bladder are coupled to each other and pressurized, with the first fluid bladder attached to a proximal side of the measurement site and the second fluid bladder attached to the distal side of the measurement site, and a computation that calculates an index that determines arteriosclerosis as the blood pressure information, based on a change in the internal pressure of the first fluid bladder when the first fluid bladder and the second fluid bladder are decoupled after it is determined that the distal side of the measurement site is in the avascularized state and the adjustment unit maintains the internal pressure of the second fluid bladder at an internal pressure at which it is determined that the distal side of the measurement site is in the avascularized state, with the first fluid bladder attached to the proximal side of the measurement site and the second fluid bladder attached to the distal side of the measurement site.

According to one or more embodiments of the present disclosure, the computation unit further executes a computation that calculates an index for use in the computation that determines the avascularized state, based on the change in the internal pressure of the at least one of the fluid bladders during the process of pressurization, with the first fluid bladder attached to the proximal side of the measurement site and the second fluid bladder attached to the distal side of the measurement site, and the computation unit determines that avascularization on the distal side of the measurement site has been completed by detecting that the index has converged during the process of pressurization.

According to one or more embodiments of the present invention, the index is at least one of a pulse wave amplitude, an AI (Augmentation Index) value that is a ratio between an amplitude of an ejection wave and an amplitude of a reflection wave, and a TR (Time of Reflection) value that is an appearance time difference between the ejection wave and the reflection wave.

According to one or more embodiments of the present invention, a control method of a blood pressure information measurement device is a control method of a blood pressure information measurement device for measuring blood pressure information of a subject using the blood pressure information measurement device. The blood pressure information measurement device includes a first fluid bladder, a second fluid bladder, and a coupling unit that switches between a coupled state in which the first fluid bladder and the second fluid bladder are coupled to each other so that communication of a fluid inside the fluid bladders is allowed and an uncoupled state in which the coupled state of the fluid bladders is released so that communication of the fluid is not allowed. The control method of the blood pressure information measurement device includes the steps of coupling and pressurizing the first fluid bladder and the second fluid bladder, with the first fluid bladder attached to a proximal side of a measurement site and the second fluid bladder attached to a distal side of the measurement site; determining an avascularized state on the distal side of the measurement site, based on a change in an internal pressure of at least one of the first fluid bladder and the second fluid bladder during the pressurizing step; decoupling the first fluid bladder and the second fluid bladder after it is determined at the step of determining the avascularized state that the distal side of the measurement site is in the avascularized state, and maintaining the internal pressure of the second fluid bladder at an internal pressure at which it is determined that the distal side of the measurement site is in the avascularized state; and calculating an index that determines arteriosclerosis as the blood pressure information, based on a change in the internal pressure of the first fluid bladder during the maintaining step.

According to one or more embodiments of the present disclosure, the control method of the blood pressure information measurement device further includes the step of calculating an index for use at the step of determining the avascularized state, based on the change in the internal pressure of the at least one of the fluid bladders during the pressurizing step, wherein at the step of determining the avascularized state, it is determined that avascularization on the distal side of the measurement site has been completed by detecting that the index has converged during the pressurizing step.

According to one or more embodiments of the present disclosure, the index is at least one of a pulse wave amplitude, an AI (Augmentation Index) value that is a ratio between an amplitude of an ejection wave and an amplitude of a reflection wave, and a TR (Time of Reflection) value that is an appearance time difference between the ejection wave and the reflection wave.

According to one or more embodiments of the present invention, the cuff is pressed against the measurement site with an optimum pressing force irrespective of the physical characteristics of the subject. Accordingly, it is possible to accurately measure the blood pressure information.

DETAILED DESCRIPTION OF INVENTION

The following describes an embodiment of the present invention with reference to the drawings. In the following description, identical parts and constituent elements will be denoted by identical reference numerals. This also applies to names and functions of those parts and constituent elements.

Figure 1:
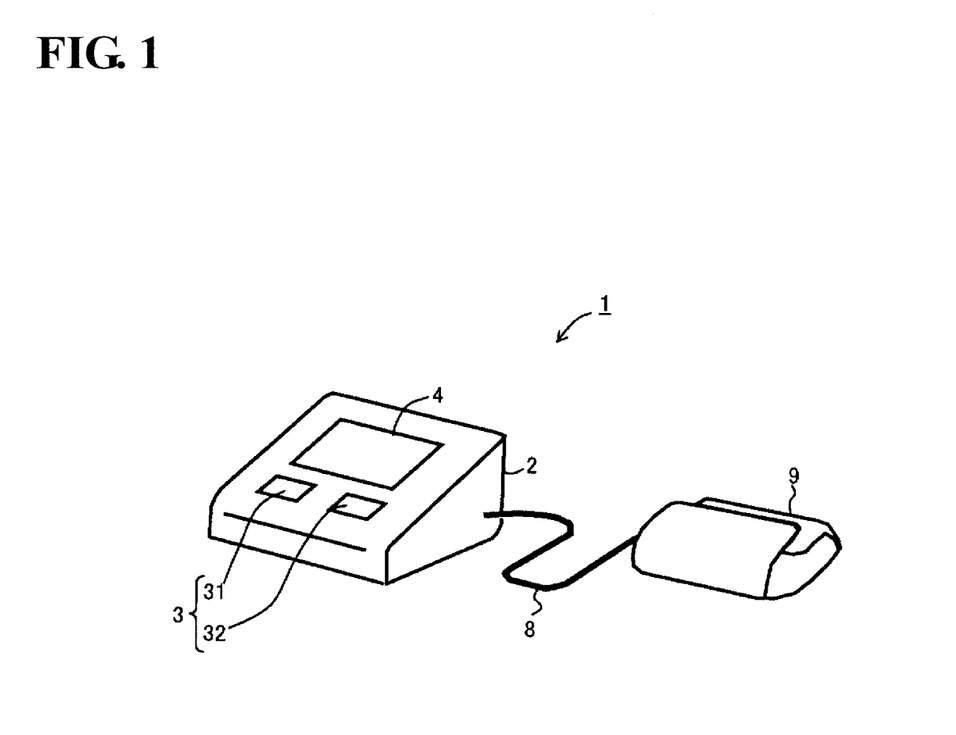
FIG. 1 is a perspective view showing a specific example of an external configuration of a measurement device according to an embodiment.

Referring to FIG. 1, a blood pressure information measurement device (hereinafter abbreviated as the measurement device) 1 of an embodiment includes a base body 2 and an arm band 9 connected to the base body 2 and to be attached to an upper arm serving as a measurement site, and these are connected to each other by an air tube 8. A display unit 4 for displaying various types of information including the measurement result and an operation unit 3 that is operated to give various instructions to the measurement device 1 are disposed at the front of the base body 2. The operation unit 3 includes a switch 31 that is operated to turn on or off a power supply and a switch 32 that is operated to give an instruction to start measurement.

Figure 2A:
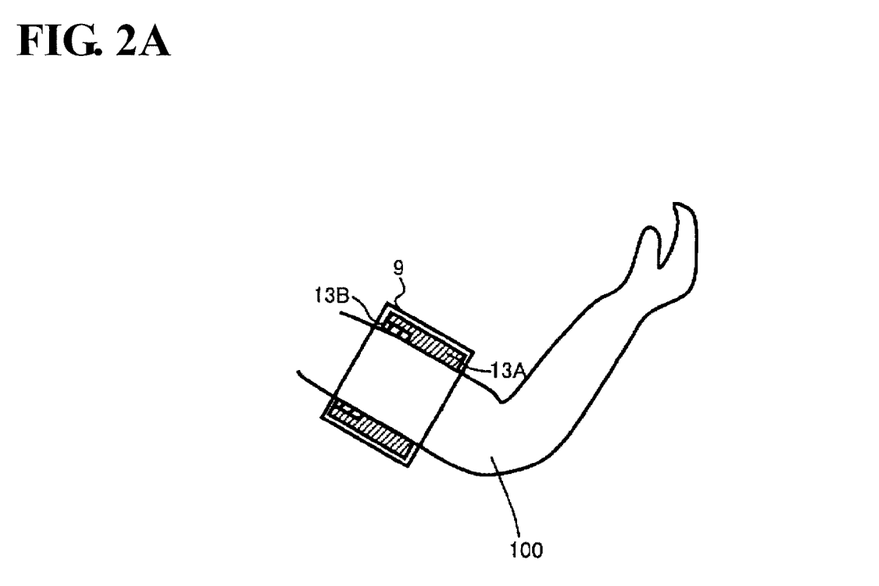
FIG. 2A is a schematic cross-sectional view showing a measurement position during measurement of blood pressure information using the measurement device.

To measure a pulse wave using the above-described measurement device 1, as shown in FIG. 2A, the arm band 9 is wrapped around an upper arm 100 serving as the measurement site. In this state, the switch 32 is pressed, and thus measurement is started.

Blood pressure information includes information such as a blood pressure value, a pulse wave waveform, and a heart rate as well as information calculated therefrom, such as a systolic blood pressure value, a diastolic blood pressure value, a pulse rate, a pulse wave amplitude, an AI (Augmentation Index: pulse wave augmentation index) value, and a TR (Time of Reflection: appearance time difference) value.

Referring to FIG. 2A, the arm band 9 contains an air bladder 13A and an air bladder 13B. When the arm band 9 is wrapped around the upper arm 100 serving as the measurement site, the air bladder 13A covers the entire measurement site, and the air bladder 13B is located on the proximal side and between the air bladder 13A and the upper arm 100. According to one or more embodiments of the present disclosure, a vibration isolating member, such as a urethane sheet, for suppressing transmission of vibrations between the air bladder 13A and the air bladder 13B is provided between these air bladders.

Figure 2B:
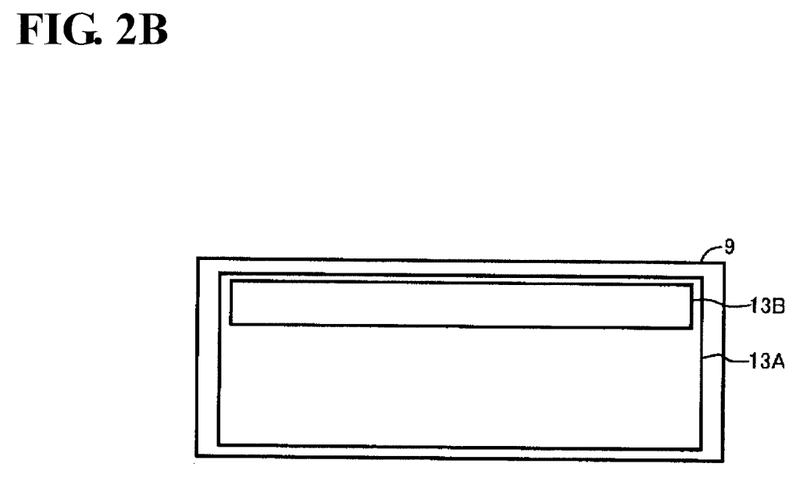
FIG. 2B is a diagram showing the configuration of an arm band.

Referring to FIG. 2B, the air bladder 13A and the air bladder 13B have substantially the same length in a longitudinal direction of the arm band 9 and have at least a length greater than or equal to the circumferential length of the upper arm 100. The ratio of the length of the air bladder 13A in a width direction of the arm band 9 to that of the air bladder 13B is about 5:1. According to one or more embodiments of the present disclosure, the air bladder 13A has the same size as the size of ordinary air bladders for use in blood pressure measurement, and the air bladder 13B has a size of 20 mm×220 mm.

Figure 3:
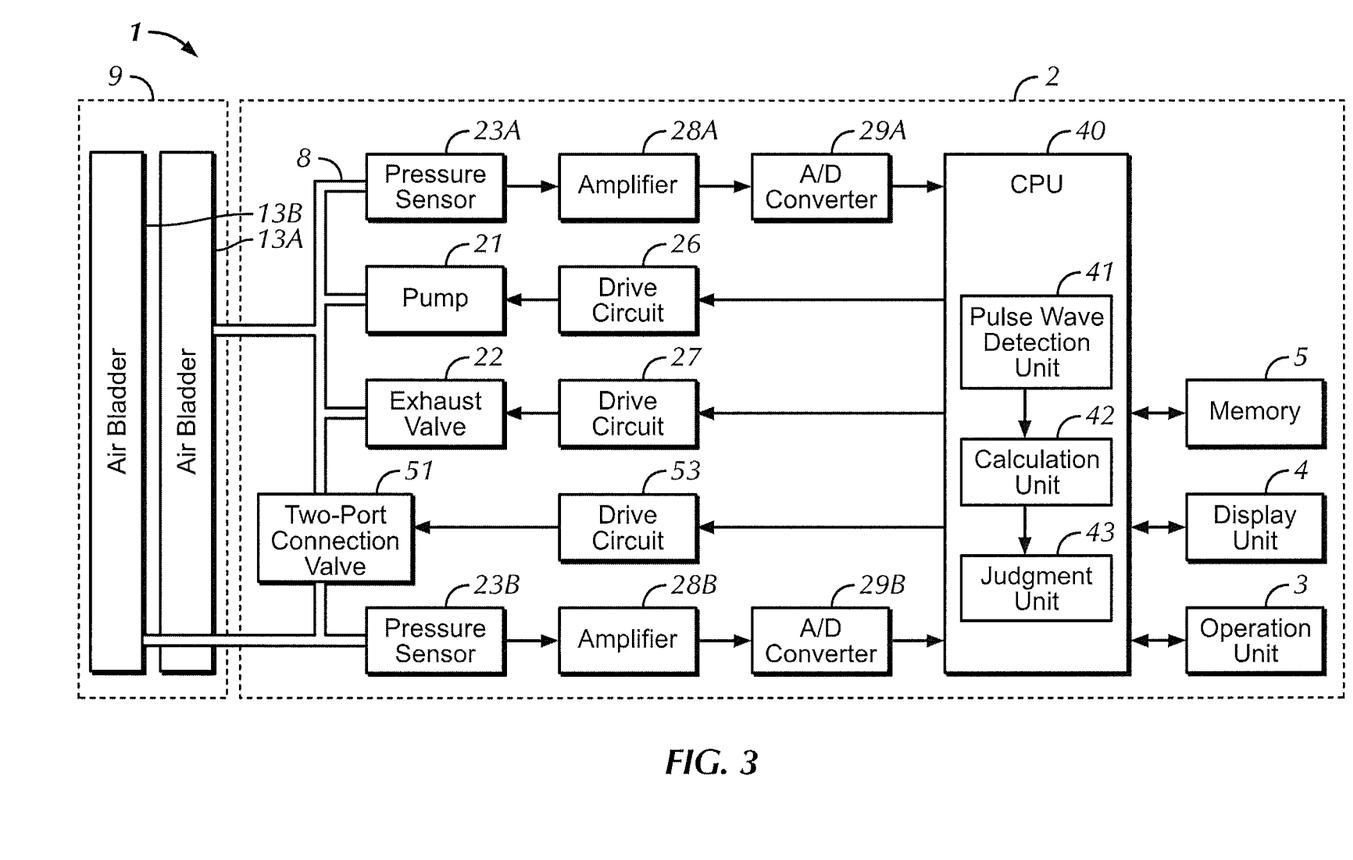
FIG. 3 is a block diagram showing the configuration of the measurement device.

Referring to FIG. 3, the base body 2 of the measurement device 1 includes a pressure sensor 23A, a pump 21, and an exhaust valve 22, which are coupled to the air bladder 13A by the air tube 8, and a pressure sensor 23B, which is coupled to the air bladder 13B by the air tube 8. The pressure sensor 23A, the pump 21, and the exhaust valve 22 are coupled to the pressure sensor 23B by the air tube 8 with a two-port connection valve 51 interposed therebetween.

The two-port connection valve 51 is connected to a drive circuit 53. The pressure sensors 23A and 23B are connected to amplifiers 28A and 28B, and the amplifiers 28A and 28B are further connected to A/D converters 29A and 29B. The pump 21 is connected to a drive circuit 26, and the exhaust valve 22 is connected to a drive circuit 27.

The drive circuit 26, the drive circuit 27, the A/D converters 29A and 29B, and the drive circuit 53 are connected to a CPU (Central Processing Unit) 40 for performing overall control of the measurement device 1. Furthermore, the display unit 4, the operation unit 3, and a memory 5 are connected to the CPU 40.

The memory 5 stores a control program and the like executed by the CPU 40. Furthermore, the memory 5 also serves as a work area for the CPU 40 to execute a program.

The CPU 40 executes a predetermined program stored in the memory 5 based on an operation signal input from the operation unit 3 and outputs control signals to the drive circuit 26, the drive circuit 27, and the drive circuit 53. The drive circuit 26, the drive circuit 27, and the drive circuit 53 respectively drive the pump 21, the exhaust valve 22, and the two-port connection valve 51 in accordance with the control signals.

Drive of the pump 21 is controlled by the drive circuit 26 in accordance with the control signal from the CPU 40 to inject air into the air bladder 13A and/or the air bladder 13B. Opening/closing of the exhaust valve 22 is controlled by the drive circuit 27 in accordance with the control signal from the CPU 40 to discharge air in the air bladder 13A and/or the air bladder 13B.

The two-port connection valve 51 has two valves, that is, a valve on the side coupled to the air bladder 13A with the pressure sensor 23A, the pump 21, and the exhaust valve 22 interposed therebetween and a valve on the side coupled to the air bladder 13B with the pressure sensor 23B interposed therebetween, and opening/closing of each valve is controlled by the drive circuit 53 in accordance with the control signal from the CPU 40. When both of the valves are opened, the air bladder 13A and the air bladder 13B are coupled to each other by the air tube 8 and form a single space. When either of the valves is closed, the air bladder 13A and the air bladder 13B each form an independent space.

The pressure sensors 23A and 23B are capacitance pressure sensors, and capacitance values thereof change as the internal pressures of the air bladders 13A and 13B change. Oscillation frequency signals corresponding to the capacitance values of the pressure sensors 23A and 23B are amplified to predetermined frequencies in the amplifiers 28A and 28B, converted into digital form by the A/D converters 29A and 29B, and then input to the CPU 40.

The CPU 40 executes predetermined processing based on changes in internal pressure of the air bladders 13A and 13B that have been obtained from the pressure sensors 23A and 23B, and outputs the above-described control signals to the drive circuit 26, the drive circuit 27, and the drive circuit 53 in accordance with the result of processing. Moreover, the CPU 40 calculates blood pressure information such as the blood pressure value and the pulse based on the changes in internal pressure of the air bladders 13A and 13B that have been obtained from the pressure sensors 23A and 23B, performs processing for displaying the measurement result on the display unit 4, and outputs data to be displayed and a control signal to the display unit 4. Moreover, the CPU 40 performs processing for storing the blood pressure information in the memory 5.

The measurement device 1 detects a pulse wave by extracting a vibration component arising from a change in the volume of an artery superposed on a change in the internal pressure of the air bladder 13B while subjecting the distal side to avascularization with the air bladder 13A in a state in which the arm band 9 is wrapped around the measurement site. Thus, an ejection wave from the heart and a reflection wave from the iliac artery bifurcation and the sclerotic site in the artery are separated from each other. The amplitude difference, the amplitude ratio, and the appearance time difference between these waves serve as indices for determination of arteriosclerosis. For this reason, the measurement device 1 calculates an AI value, which is expressed as an amplitude ratio between the ejection wave and the reflection wave, or a TR value as an arteriosclerosis index.

Figure 4A:
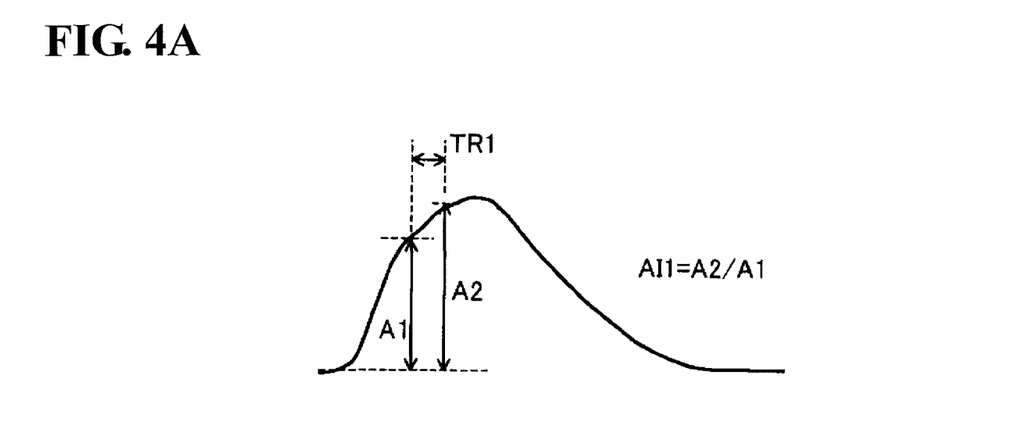
FIG. 4A is a diagram showing an example of a pulse wave that is detected when a pressing force on the distal side of a measurement site has been changed.
Figure 4B:
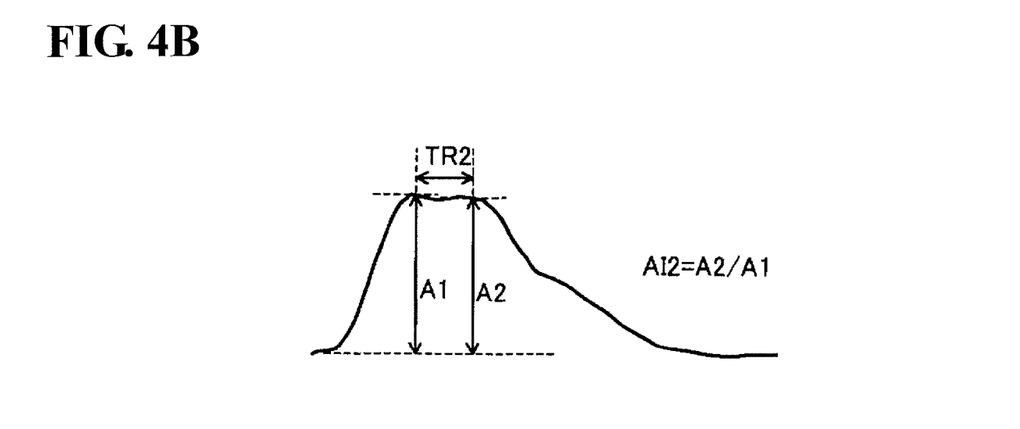
FIG. 4B is a diagram showing an example of a pulse wave that is detected when the pressing force on the distal side of the measurement site has been changed.
Figure 4C:
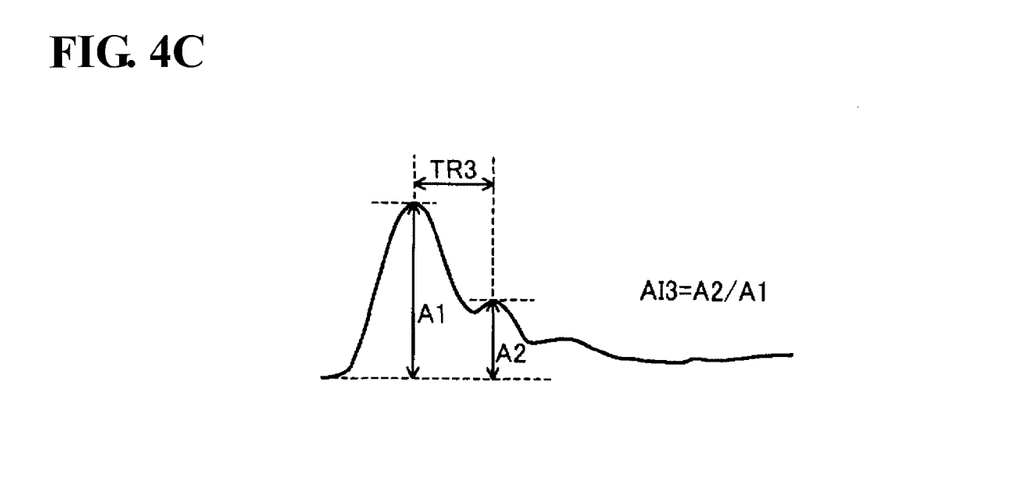
FIG. 4C is a diagram showing an example of a pulse wave that is detected when the pressing force on the distal side of the measurement site has been changed.

The shape of the measured pulse wave varies as shown in FIGS. 4A to 4C depending on the extent of avascularization on the distal side. That is to say, if the pressing force on the distal side is low, the reflection wave from a distal area is superposed on the pulse wave as shown in FIG. 4A. Accordingly, AI1, which is the amplitude ratio (AI value) between the ejection wave and the reflection wave at this time, increases, and TR1, which is the appearance time difference (TR value) between the ejection wave and the reflection wave, decreases.

As the pressing force on the distal side increases, the superposition of reflection from the distal area decreases as shown in FIG. 4B. Consequently, AI2 is smaller than AI1 and TR2 is greater than TR1.

Once the distal side is completely avascularized, reflection from the distal area is no longer superposed as shown in FIG. 4C. Consequently, only the reflection wave from the iliac artery bifurcation and the sclerotic site in the artery, which serve as the measurement target, is detected.

Figure 5A:
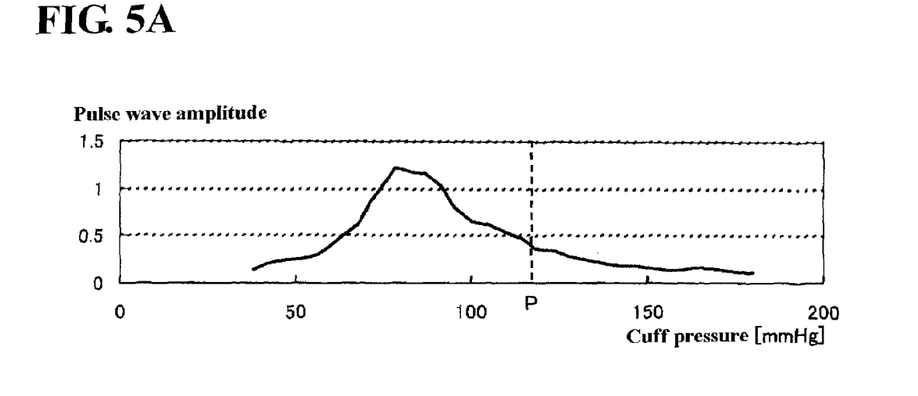
FIG. 5A is a diagram showing changes in a pulse wave amplitude obtained from the detected pulse wave when the pressing force on the distal side of the measurement site has been changed.
Figure 5B:
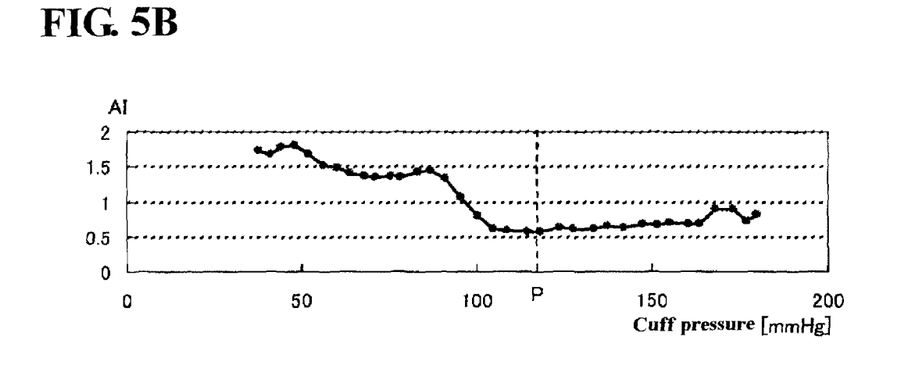
FIG. 5B is a diagram showing changes in an AI (Augmentation Index: pulse wave augmentation index) value obtained from the detected pulse wave when the pressing force on the distal side of the measurement site has been changed.
Figure 5C:
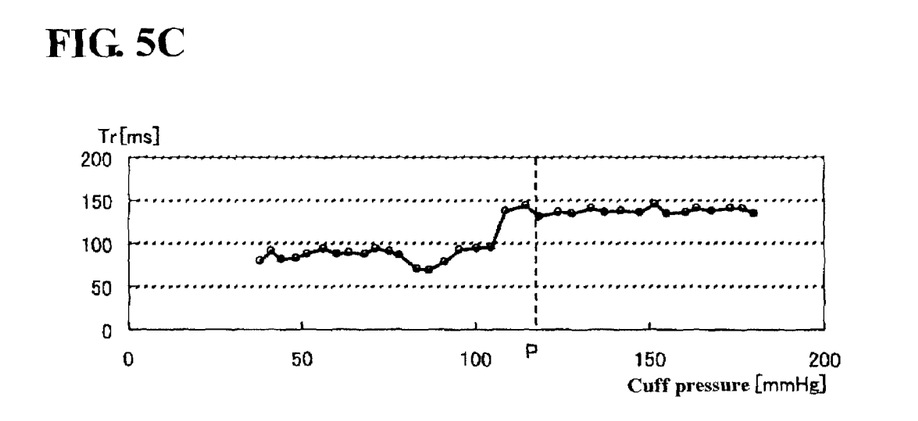
FIG. 5C is a diagram showing changes in a TR (Time of Reflection: appearance time difference) value obtained from the detected pulse wave when the pressing force on the distal side of the measurement site has been changed.

Using the measurement device 1, the inventors of the present invention detected a pulse wave while changing the pressures in the air bladders 13A and 13B, calculated changes in the pulse wave amplitude, the AI value, and the TR value, and obtained the result shown in FIG. 5A as the changes in the pulse wave amplitude corresponding to the changes in internal pressure of the air bladders, the result shown in FIG. 5B as the changes in the AI value corresponding to the changes in internal pressure of the air bladders, and the result shown in FIG. 5C as the changes in the TR value corresponding to the changes in internal pressure of the air bladders. That is to say, it was verified that although all of the pulse wave amplitude, the AI value, and the TR value change with the changes in internal pressure of the air bladders until an avascularized state is reached, once the avascularized state is reached, these values converge at substantially fixed values even if the internal pressures of the air bladders further increase from an internal pressure P at the time when the avascularized state has been reached. This is because the reflection wave component does no longer change even if the internal pressures of the air bladders further increase in the avascularized state. This result verified that it is possible to determine the avascularized state on the distal side using convergence of the pulse wave amplitude, the AI value, or the TR value.

Referring again to FIG. 3, the CPU 40 of the measurement device 1 includes a pulse wave detection unit 41, a calculation unit 42, and a judgment unit 43 as components for determining the avascularized state on the distal side using the convergence of the pulse wave amplitude, the AI value, or the TR value. These components are functions formed mainly on the CPU 40 by the CPU 40 reading and executing the above-described control program stored in the memory 5 in accordance with the operation signal from the operation unit 3, but at least a part of these functions may also be formed by the hardware components shown in FIG. 3.

Figure 6:
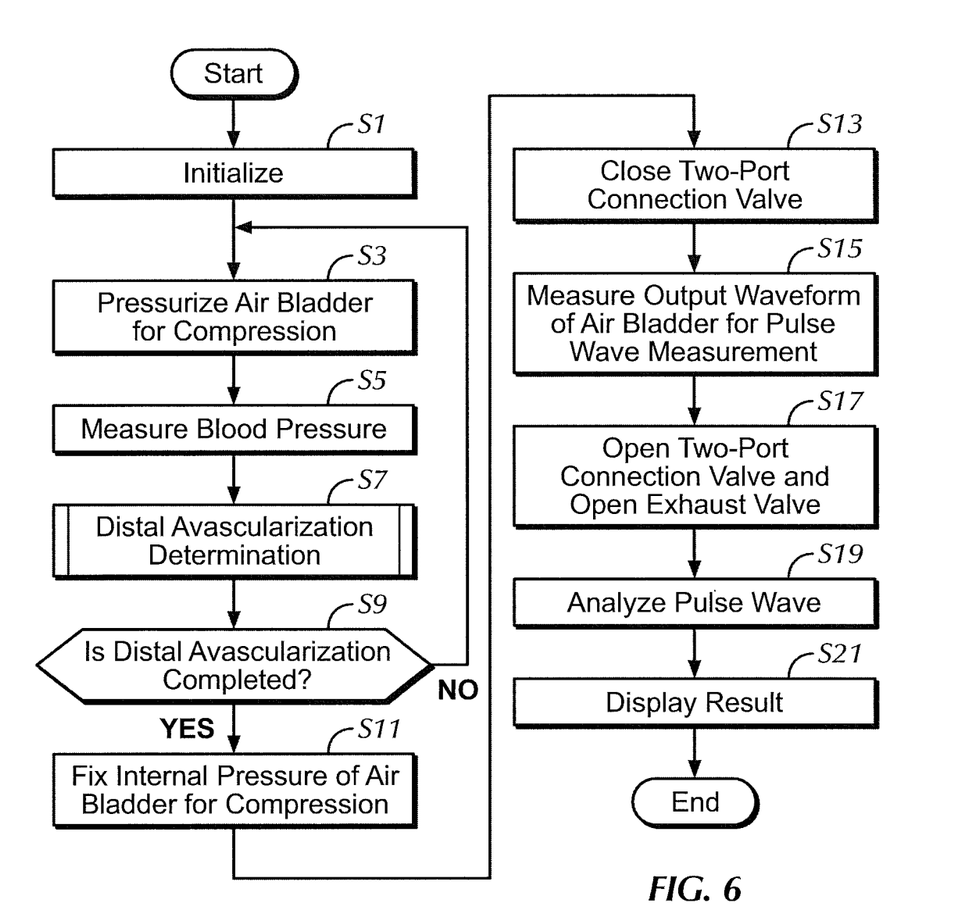
FIG. 6 is a flowchart illustrating a measurement operation of the measurement device.
Figure 8:
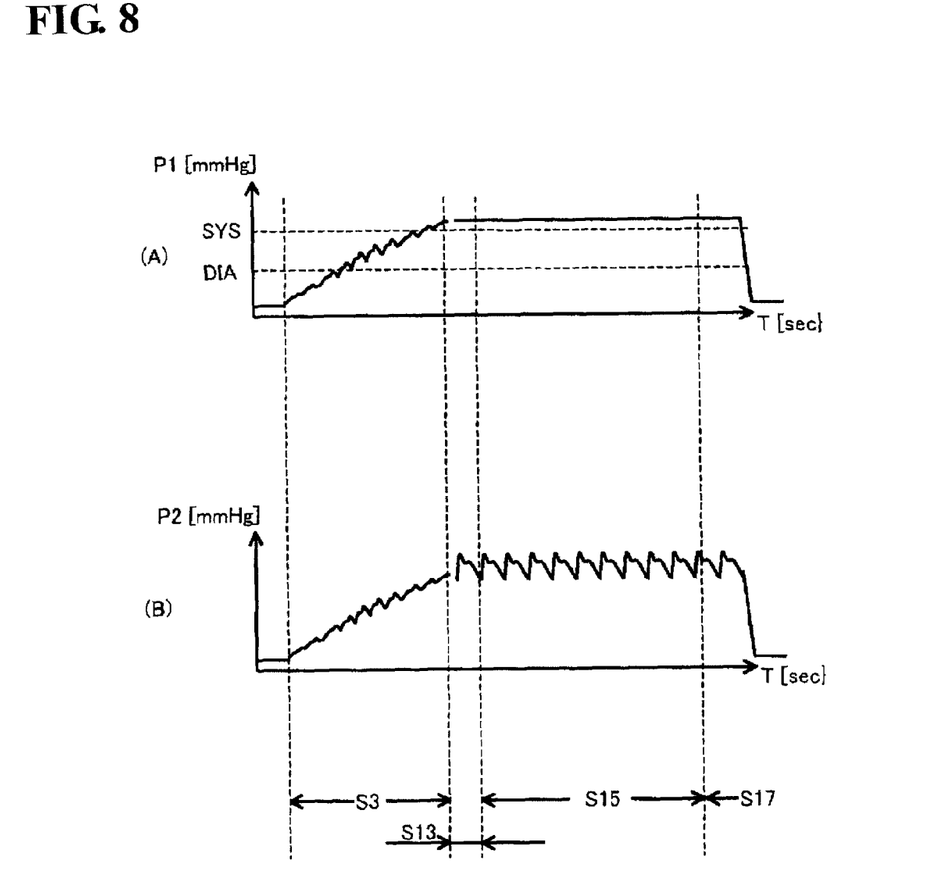
FIG. 8 is a diagram showing changes in internal pressure of air bladders during the measurement operation of the measurement device.

A measurement operation of the measurement device 1 will be described using FIG. 6. The operation illustrated in the flowchart in FIG. 6 is started as a result of the switch 31 being pressed, and implemented by the CPU 40 reading the control program stored in the memory 5 and controlling the units shown in FIG. 3. Moreover, FIG. 8 shows changes in an internal pressure P1 of the air bladder 13A and an internal pressure P2 of the air bladder 13B with the progress of the measurement operation.

Referring to FIG. 6, once the measurement operation is started, the CPU 40 initializes the units at step S1, and then, at step S3, outputs a control signal to the drive circuit 26 to actuate and cause the pump 21 to pressurize the air bladder 13A serving as an air bladder for compression. During the initialization at step S1, the CPU 40 outputs a control signal to the drive circuit 53 to open both of the valves of the two-port connection valve 51. Thus, as shown in FIG. 8, both the internal pressure P1 of the air bladder 13A and the internal pressure P2 of the air bladder 13B increase as the pump 21 introduces compressed air at step S3.

During the process of pressurization, at step S5, the CPU 40 extracts a vibration component arising from a change in the volume of the artery superposed on the internal pressure of the air bladder 13A and calculates a blood pressure value by a predetermined computation. The method of calculating the blood pressure value herein may be a calculation method that uses oscillometry employed in ordinary electronic sphygmomanometers. At the same time, at step S7, the CPU 40 performs processing for determining the avascularized state on the distal side.

Figure 7:
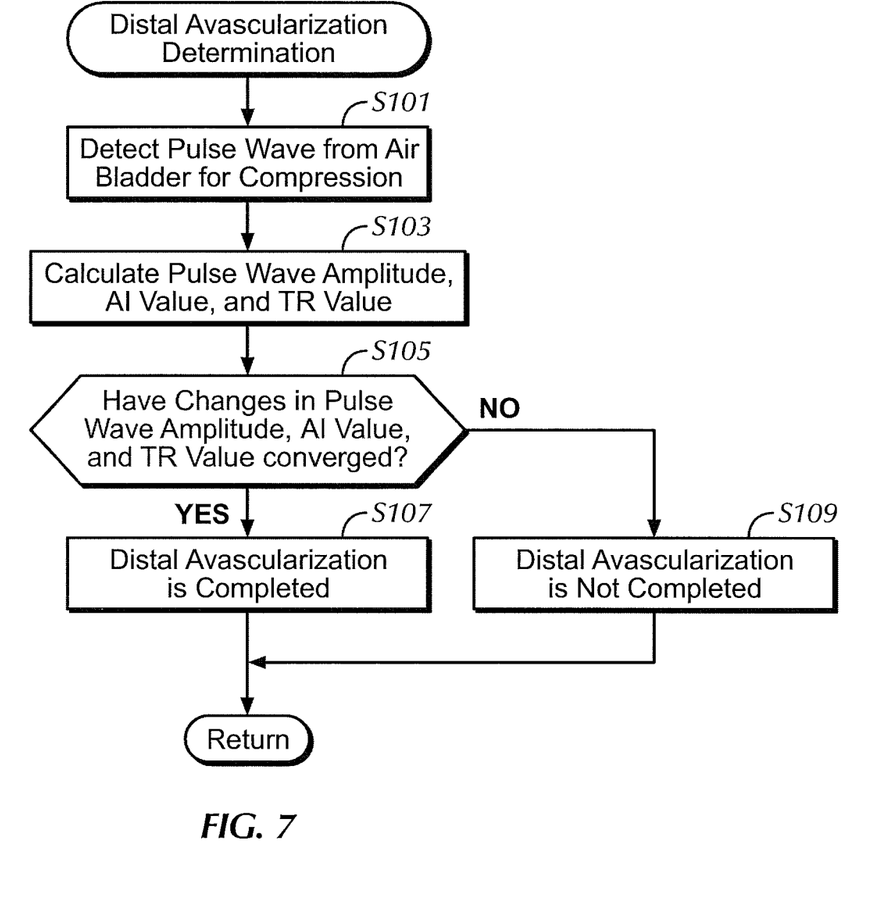
FIG. 7 is a flowchart illustrating processing for determining an avascularized state on the distal side.

The determination processing at step S7 will be described with reference to FIG. 7. At step S101, the pulse wave detection unit 41 detects a pulse wave from the vibration component arising from the change in the volume of the artery superposed on the internal pressure of the air bladder 13A. At step S103, the calculation unit 42 calculates an index value for use in determination of the avascularized state, from the beat-by-beat pulse wave. Here, in order to determine the avascularized state using the above-described principle, any of the pulse wave amplitude, the AI value, and the TR value is calculated as the index value. The calculated index value is temporarily stored.

The judgment unit 43 of the CPU 40 judges whether or not the index value calculated at step S103 has converged. An example of a specific judgment method is a method in which the index value calculated at step S103 is compared with an index value that has been previously calculated and temporarily stored, and it is judged that the index value has converged if the difference is less than a threshold (for example, 10% of an average of two beats) that is stored in advance.

If the judgment unit 43 judges that the index value has converged (YES at step S105), at step S107, the CPU 40 returns the result that avascularization on the distal side has been completed. If not (NO at step S105), the CPU 40 returns the result that avascularization on the distal side is not completed yet.

Note that although it is assumed in the example above that any one index of the pulse wave amplitude, the AI value, and the TR value is used for determination, it is also possible that two or more of these indices are used, and it is determined that avascularization is not completed yet if even one of the indices used has not converged and it is determined that avascularization has been completed if it is judged that all of the indices used have converged. The use of a plurality of indices can enhance the determination accuracy even more.

Furthermore, it is assumed in the example above that, in the determination at step S7, the index value for use in determination is calculated based on the internal pressure of the air bladder 13A, but the internal pressure of the air bladder 13B may be used in the determination at step S7, or the internal pressures of both of the air bladders 13A and 13B may be used. The reason for this is that because, in the pressurization process, the pump 21 is actuated with both of the valves of the two-port connection valve 51 open as described above, the air bladders 13A and 13B are pressurized as a single unit, and the internal pressures of the two air bladders are equal. The use of the internal pressure of the air bladder 13B instead of the internal pressure of the air bladder 13A in the determination at step S7 can eliminate the need for a mechanism (such as the internal pressure sensor 23B) for measuring the internal pressure of the air bladder 13B.

As long as it is determined at step S7 that avascularization on the distal side is not completed yet (NO at step S9), the CPU 40 repeats pressurization of the air bladder 13A at step S3 and determination at step S7. Thus, as shown in FIG. 8, both of the internal pressure P1 of the air bladder 13A and the internal pressure P2 of the air bladder 13B increase until avascularization on the distal side is completed.

If it is determined in the determination at step S7 that avascularization on the distal side has been completed (YES at step S9), at step S11, the CPU 40 outputs a control signal to the drive circuit 26 to stop pressurization and fixes the internal pressure of the air bladder 13A. Subsequently, at step S13, the CPU 40 outputs a control signal to the drive circuit 53 to close both of the valves of the two-port connection valve 51. Thus, the air bladder 13A and the air bladder 13B form separate spaces, and because the air bladder 13A maintains the internal pressure at which it is determined that avascularization on the distal side has been completed and compresses the measurement site, the avascularized state is maintained in an area distal to the air bladder 13B for use in pulse wave detection. That is to say, the air bladder 13A functions as the air bladder for compression.

Figure 9:
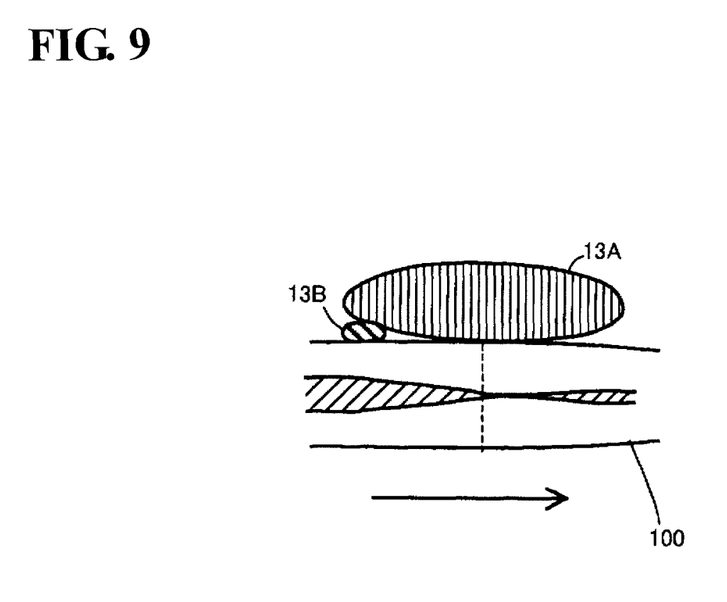
FIG. 9 is a diagram for explaining pressing of the air bladders against the measurement site.

Because the air bladder 13A inflates in the direction of the artery into the shape of an ellipse, a center portion thereof touches the measurement site with the greatest pressure, and the pressing force by the air bladder 13A is the highest at the center portion. If it is determined in the determination at step S7 that the distal side is in the avascularized state, as shown in FIG. 9, the pressing force of the center portion of the air bladder 13A is higher than the systolic blood pressure, and the artery located immediately under that portion is flattened. At positions away from the position immediately under the center of the air bladder 13A, the artery is not completely flattened as shown in FIG. 9 because the pressing force from the air bladder 13A gradually weakens at those positions.

As also shown in FIG. 2A, the air bladder 13B is located proximal to the center portion of the air bladder 13A when the arm band 9 is attached to the upper arm 100, and the artery is not completely flattened at that position as described above. Moreover, as also shown in FIG. 2B, because the volume of the air bladder 13B is smaller than the volume of the air bladder 13A, the air bladder 13B has the higher sensitivity to superposition of the change in the volume of the artery on the internal pressure. Therefore, as shown in FIG. 8, after avascularization on the distal side has been completed and the two-port connection valve 51 has been closed at step S13, the pulse wave is not superposed on the internal pressure P1 of the air bladder 13A and a higher internal pressure than the systolic blood pressure is maintained ((A) in FIG. 8), but the pulse wave is superposed on the internal pressure P2 of the air bladder 13B. At step S15, an output waveform is measured from the vibration component of the internal pressure of the air bladder 13B which is shown in FIG. 8 and on which the pulse wave is superposed ((B) in FIG. 8), and the pulse wave is detected.

Then, at step S17, the CPU 40 outputs a control signal to the drive circuit 53 to open the two-port connection valve 51 and, furthermore, outputs a control signal to the drive circuit 27 to open the exhaust valve 22, so that air is quickly exhausted from the air bladders 13A and 13B. Thus, as shown in FIG. 8, the internal pressures P1 and P2 of the air bladders 13A and 13B quickly return to the atmospheric pressure after step S17.

At step S19, the CPU 40 analyzes the pulse wave detected at step S15 and calculates the AI value, the TR value, or the like serving as an index of arteriosclerosis. Then, at step S21, the CPU 40 executes processing for displaying the blood pressure value measured at step S5, the index calculated at step S19, and the like on the display unit 4 as the measurement result, and finishes a series of procedures of the measurement operation.

Here, the rate at which the pressing force (internal pressure) of the air bladder 13A is transferred to the artery is regarded as the "transfer efficiency" and defined as follows:

Transfer efficiency=internal pressure when pulse wave on distal side disappears/systolic blood pressure measured by air bladder attached to upper arm In cases where 100% of the internal pressure is transferred to the artery, that is, the transfer efficiency is 1, if the artery is pressed against with a pressure equal to the systolic blood pressure, the artery is completely occluded, and the pulse wave in an area distal to the pressed portion disappears. However, generally, due to the influence of the muscles and fat that are present around the artery, there is no case where 100% of the internal pressure of the air bladder 13A is transferred to the artery, and a pressing force higher than the systolic blood pressure is necessary to occlude the artery. For this reason, the transfer efficiency is affected by physical characteristics of the subject, such as the amount of muscle, the amount of fat, and the depth of the artery. Note that to measure the internal pressure of the air bladder at the time when the pulse wave on the distal side disappears, for example, in a state in which a photoelectric pulse wave sensor is attached to a fingertip, the upper arm is pressed against by the air bladder attached thereto with gradually increasing pressure, and an internal pressure at the time when the pulse wave amplitude disappears or becomes lower than a predetermined threshold (e.g., 10% of the pulse wave amplitude before pressing) is measured.

With a uniform pressing force as employed in the conventional devices, such as a predefined pressing force or a pressing force set by adding a predefined pressure to the systolic blood pressure value of the subject, there are cases where the transfer efficiency is lower than expected depending on the above-described physical characteristics of the subject, and in such cases, the pressing force is insufficient. Alternatively, there are cases where the transfer efficiency is higher than expected, and in such cases, the pressing force is excessive.

In contrast, the measurement device 1 judges the avascularized state on the distal side based on convergence of an index value such as the pulse wave amplitude, the AI value, or the TR value and therefore can achieve the avascularized state using a suitable pressing force without being affected by the physical characteristics of the subject, such as the amount of muscle, the amount of fat, and the depth of the artery. Thus, the characteristic point of the ejection wave and the characteristic point of the reflection wave can be precisely detected without being affected by the physical characteristics of the subject, or in other words, even for subjects having different transfer efficiencies. Accordingly, the arteriosclerosis level can be accurately determined. Also, the burden on the subject can be reduced.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 measurement device
2 base body
3 operation unit
4 display unit
5 memory
8 air tube
9 arm band
13A, 13B air bladder
21 pump
22 exhaust valve
23A, 23B pressure sensor
26, 27, 53 drive circuit
28A, 28B amplifier
29A, 29B A/D converter
31, 32 switch
40 CPU
41 pulse wave detection unit
42 calculation unit
43 judgment unit
51 two-port connection valve

The invention claimed is:

1. A blood pressure information measurement device for measuring blood pressure information of a subject, comprising:
a first fluid bladder;
a second fluid bladder;
a two-port connection valve inserted in a tube between the first fluid bladder and the second fluid bladder, wherein the two-port connection valve switches between a coupled state in which the first fluid bladder and the second fluid bladder are coupled to each other so that communication of a fluid inside the first and second fluid bladders is allowed and an uncoupled state in which the coupled state of the first and second fluid bladders is released so that communication of the fluid is not allowed;

an adjustment unit comprising an air pump and a valve that adjusts internal pressures of the first fluid bladder and the second fluid bladder;

a first pressure sensor that measures the internal pressure of the first fluid bladder;

a second pressure sensor that measures the internal pressure of the second fluid bladder; and a computation unit that is programmed to calculate blood pressure information based on a change in the internal pressure of each of the first fluid bladder and the second fluid bladder attached to a measurement site, the computation unit being programmed to execute:
a computation that determines an avascularized state on a distal side of the measurement site, concurrently with a change in the internal pressure of at least one of the first fluid bladder and the second fluid bladder during a process by which the two-port connection valve is switched to the coupled state so that the first fluid bladder and the second fluid bladder are coupled to each other and pressurized, with the first fluid bladder attached to a proximal side of the measurement site and the second fluid bladder attached to the distal side of the measurement site, and a computation that calculates an index that determines arteriosclerosis as the blood pressure information, based on a change in the internal pressure of the first fluid bladder when the two-port connection valve is switched to the uncoupled state so that the first fluid bladder and the second fluid bladder are decoupled after it is determined that the distal side of the measurement site is in the avascularized state and the adjustment unit maintains the internal pressure of the second fluid bladder at an internal pressure at which it is determined that the distal side of the measurement site is in the avascularized state, with the first fluid bladder attached to the proximal side of the measurement site and the second fluid bladder attached to the distal side of the measurement site.

2. The blood pressure information measurement device according to claim 1,
wherein the computation unit is further programmed to execute a computation that calculates an index for use in the computation that determines the avascularized state, based on the change in the internal pressure of the at least one of the fluid bladders during the process of pressurization, with the first fluid bladder attached to the proximal side of the measurement site and the second fluid bladder attached to the distal side of the measurement site, and
wherein the computation unit determines that avascularization on the distal side of the measurement site has been completed by detecting that the index has converged during the process of pressurization.

3. The blood pressure information measurement device according to claim 2, wherein the index is at least one of a pulse wave amplitude, an AI (Augmentation Index) value that is a ratio between an amplitude of an ejection wave and an amplitude of a reflection wave, and a TR (Time of Reflection) value that is an appearance time difference between the ejection wave and the reflection wave.

4. A control method of a blood pressure information measurement device for measuring blood pressure information of a subject using the blood pressure information measurement device,
the blood pressure information measurement device comprising:
a first fluid bladder;
a second fluid bladder; and
a two-port connection valve inserted in a tube between the first fluid bladder and the second fluid bladder, wherein the two-port connection valve switches between a coupled state in which the first fluid bladder and the second fluid bladder are coupled to each other so that communication of a fluid inside the first and second fluid bladders is allowed, and an uncoupled state in which the coupled state of the first and second fluid bladders is released so that communication of the fluid is not allowed,
the method comprising the steps of:
switching the two-port connection valve to the coupled state so that the first fluid bladder and the second fluid bladder are coupled to each other and pressurized, with the first fluid bladder attached to a proximal side of a measurement site and the second fluid bladder attached to a distal side of the measurement site;
determining an avascularized state on the distal side of the measurement site, concurrently with a change in an internal pressure of at least one of the first fluid bladder and the second fluid bladder during the pressurizing step;
switching the two-port connection valve to the uncoupled state so that the first fluid bladder and the second fluid bladder are decoupled after it is determined at the step of determining the avascularized state that the distal side of the measurement site is in the avascularized state, and maintaining the internal pressure of the second fluid bladder at an internal pressure at which it is determined that the distal side of the measurement site is in the avascularized state; and
calculating with the blood pressure information measurement device an index that determines arteriosclerosis as the blood pressure information, based on a change in the internal pressure of the first fluid bladder during the maintaining step.

5. The control method of the blood pressure information measurement device according to claim 4, further comprising the step of:
calculating an index for use at the step of determining the avascularized state, based on the change in the internal pressure of the at least one of the fluid bladders during the pressurizing step,
wherein at the step of determining the avascularized state, it is determined that avascularization on the distal side of the measurement site has been completed by detecting that the index has converged during the pressurizing step.

6. The control method of the blood pressure information measurement device according to claim 5, wherein the index is at least one of a pulse wave amplitude, an AI (Augmentation Index) value that is a ratio between an amplitude of an ejection wave and an amplitude of a reflection wave, and a TR (Time of Reflection) value that is an appearance time difference between the ejection wave and the reflection wave.

* * * * *